United States Patent [19]
Siemers

[11] Patent Number: 6,029,975
[45] Date of Patent: *Feb. 29, 2000

[54] PSYCHO-SOCIAL GAME THAT MEASURES EMOTIONAL DISTANCE BETWEEN PLAYERS' RESPONSES

[76] Inventor: Donna L. Siemers, E. 11125 Day. Mt. Spokane Road, Mead, Wash. 99021

[*] Notice: This patent issued on a continued prosecution application filed under 37 CFR 1.53(d), and is subject to the twenty year patent term provisions of 35 U.S.C. 154(a)(2).

[21] Appl. No.: 08/584,158

[22] Filed: Jan. 11, 1996

Related U.S. Application Data

[63] Continuation of application No. 08/176,802, Jan. 3, 1994.

[51] Int. Cl.$^7$ .................................................. A63F 3/02
[52] U.S. Cl. ................................................. 273/242
[58] Field of Search ................... 273/242, 243, 273/248, 249

[56] References Cited

U.S. PATENT DOCUMENTS

| | | | |
|---|---|---|---|
| 3,764,135 | 10/1973 | Madison | 273/1 R |
| 4,013,294 | 3/1977 | Smeda et al. | 273/243 X |
| 4,124,214 | 11/1978 | Pavis | 273/243 X |
| 4,216,594 | 8/1980 | Farley et al. | 273/243 X |
| 4,216,971 | 8/1980 | Lyke | 273/243 |
| 4,230,320 | 10/1980 | Crew | 273/243 |
| 4,230,321 | 10/1980 | Smith | 273/308 |
| 4,234,185 | 11/1980 | Alsip | 273/243 |
| 4,244,577 | 1/1981 | Poulos | 273/236 |
| 4,273,337 | 6/1981 | Carrera et al. | 273/243 |
| 4,344,625 | 8/1982 | Frudakis | 273/242 |
| 4,354,844 | 10/1982 | Ickinger | 434/237 |
| 4,372,559 | 2/1983 | Summers | 273/243 |
| 4,508,353 | 4/1985 | Meyer et al. | 273/313 |
| 4,618,146 | 10/1986 | Yoshida et al. | 273/1 E |
| 4,741,539 | 5/1988 | Sutton et al. | 273/275 |
| 4,813,681 | 3/1989 | Volpert | 273/271 |
| 4,846,479 | 7/1989 | Hanley | 273/236 |
| 4,893,819 | 1/1990 | Wright | 273/243 |
| 4,909,740 | 3/1990 | Rankin | 434/238 |
| 5,020,804 | 6/1991 | Weedman | 273/249 |
| 5,037,305 | 8/1991 | Aleck | 434/262 |
| 5,054,775 | 10/1991 | Banks et al. | 273/431 |
| 5,108,115 | 4/1992 | Berman et al. | 273/439 |
| 5,178,544 | 1/1993 | Aleck | 434/262 |

FOREIGN PATENT DOCUMENTS

| | | | |
|---|---|---|---|
| 3800221 | 7/1989 | Germany | 273/243 |
| 2215222 | 9/1989 | United Kingdom | 273/243 |

OTHER PUBLICATIONS

Paper on "A Set of Categories for the Analysis of Small Group Interaction", Robert F. Bales, American Sociological Review, pp. 257–263.

*Primary Examiner*—Jeanette Chapman
*Assistant Examiner*—Vishu K. Mendiratta
*Attorney, Agent, or Firm*—R. Reams Goodloe, Jr.

[57] ABSTRACT

A method for determining the emotional distance between individuals. A method of evaluating the emotional distance between individuals is described by use of a game process wherein the players are provided with a number of hypothetical human interaction situations, offered a set of possible responses for each situation, and are also given an opportunity to create unique responses. A coding system is provided for prepared responses, and a response coding flow sheet is provided for determining the behavior category of the players's response. Players each set forth their response behavior code on the game board. The majority response is established, and the distance of each individual from the majority is determined. The method includes a scorekeeping system for determining the emotional distance between players responses. The method includes providing to the player a game score for the player's response selection wherein the value of the game score is based upon the player's ability to take the role of the other, i.e., the ability to respond to the same board position or behavior category. The winner of the game process is the player whose response choices express the least emotional distance between his response choices and the response choices of the other players.

39 Claims, 5 Drawing Sheets

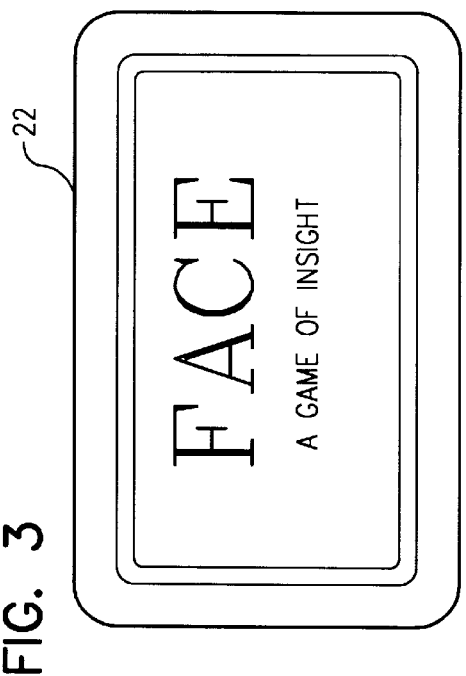
FIG. 3
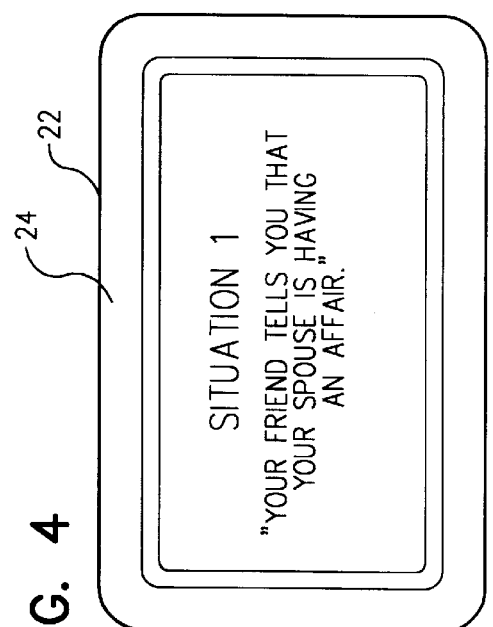
FIG. 4
FIG. 2
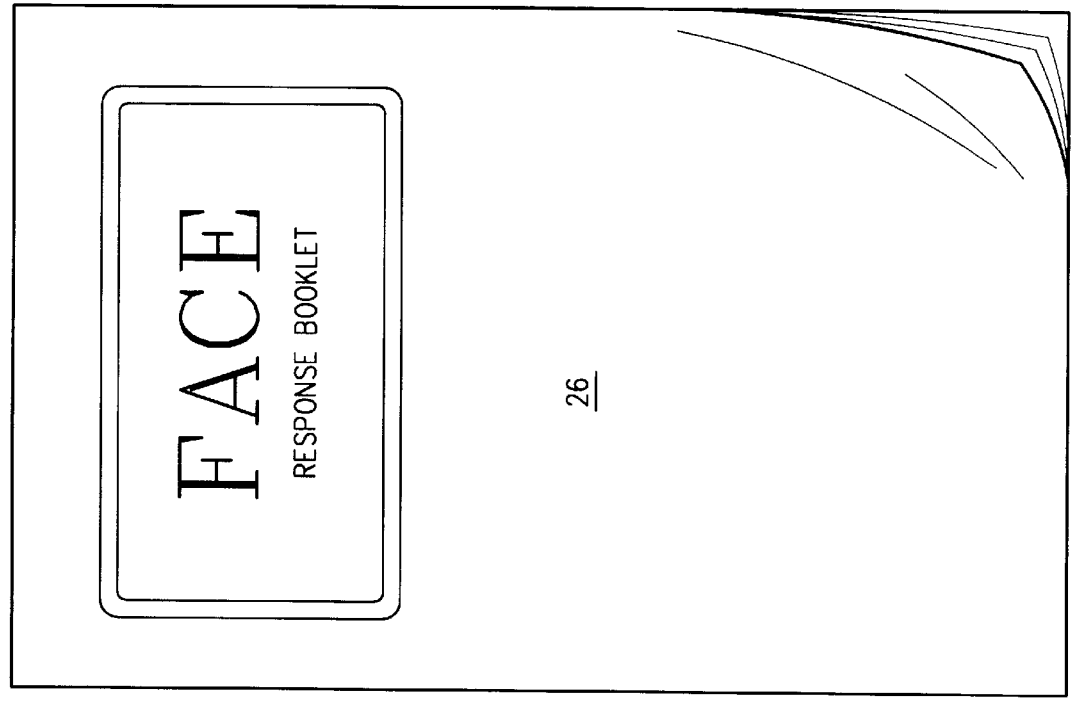

FIG. 6A

SCORE SHEET

DATE ___/___/19___          PARTICIPANT NUMBER: _____

SOCIAL CHARACTERISTICS: PLEASE WRITE IN YOUR OCCUPATION AND MARK YOUR SEX, AGE, INCOME, RACE, MARITAL STATUS AND HIGHEST LEVEL OF EDUCATION:

OCCUPATION:                                         SEX: ☐ MALE ☐ FEMALE

AGE: ☐ UNDER 25  ☐ 25-34  ☐ 35-44  ☐ 45-54  ☐ 55-64  ☐ 65-74  ☐ 75+

INCOME: ☐ LESS THAN $10,000  ☐ $10,000-19,999  ☐ $20,000-34,999
        ☐ $35,000-59,999  ☐ $60,000+

RACE: ☐ CAUCASIAN  ☐ HISPANIC  ☐ ASIAN  ☐ NATIVE AMERICAN  ☐ BLACK
      ☐ OTHER:

MARITAL STATUS: ☐ NEVER  ☐ MARRIED  ☐ SEPARATED  ☐ DIVORCED  ☐ WIDOWED
                ☐ OTHER

EDUCATION: ☐ GRADE SCHOOL  ☐ HIGH SCHOOL  ☐ SOME COLLEGE  ☐ B.A.
           ☐ MA.  ☐ PhD.

| CARD | CODE | RESPONSE |
|------|------|----------|
| 1    |      |          |
| 2    |      |          |
| 3    |      |          |
| 4    |      |          |
| 5    |      |          |
| 6    |      |          |
| 7    |      |          |
| 8    |      |          |
| 9    |      |          |
| 10   |      |          |
| 11   |      |          |
| 12   |      |          |

FIG. 6B

| CARD | CODE | RESPONSE |
|---|---|---|
| 13 | | |
| 14 | | |
| 15 | | |
| 16 | | |
| 17 | | |
| 18 | | |
| 19 | | |
| 20 | | |
| 21 | | |
| 22 | | |
| 23 | | |
| 24 | | |
| 25 | | |

I. DIVIDE TOTAL DISTANCE POINTS___ BY TOTAL FACE POINTS___ TO FIND YOUR RATIO.

II. FACE POINTS INDICATE THE NUMBER OF TIMES THAT A PLAYER TOOK THE ROLE OF THE MAJORITY, DURING THE GAME.

III. DISTANCE POINTS MEASURE THE DIFFERENCE IN EMOTIONAL INTENSITY BETWEEN THE RESPONSES OF THE MAJORITY AND THE RESPONSES OF THE INDIVIDUAL PLAYER

IV. THE WINNER IS THE PLAYER WITH THE LOWEST RATIO OF DISTANCE POINTS TO TO FACE POINTS.

SAVE YOUR USED SCORE SHEETS!

FOR A FREE REPLACEMENT PAD OF SCORE SHEETS, SEND 40 PROPERLY COMPLETED SCORE SHEETS TO:

D. L. SIEMERS
11125 E. DAY MT. SPOKANE RD.
MEAD, WA 99021

(509) 238-6242

PSYCHO-SOCIAL GAME THAT MEASURES EMOTIONAL DISTANCE BETWEEN PLAYERS' RESPONSES

This application is a continuation of copending application(s) Ser. No. 08/176,802 filed on Jan. 3, 1994.

A portion of the disclosure of this patent document contains material which is subject to copyright protection. The owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

This invention relates to methods for measurement of the emotional distance between individuals in given situations of human interaction, and to games which utilize such methods.

BACKGROUND OF THE INVENTION

Sociologists and psychologists have long recognized that a relationship exists between socially-deviant behavior and the lack of roletaking ability of the individuals exhibiting such behavior. More particularly, psychologists have long recognized that child development, both intellectually and emotionally, is in part dependent upon the roletaking capacities of their parents and teachers. Further, it has been recognized that the satisfactory and successful conduct of affairs in the adult world, especially in the area of communication and negotiation, is facilitated where the participants in a particular affair have the ability to take on the role of the other participants and to respond in such situations on the same emotional level as the other participants.

The study of roletaking, particularly with a view towards the establishment of systematic methods for development and measurement of roletaking ability, has thus been an important concern of sociological and psychological research. One method for such measurement that to some remote extent resembles the method disclosed and claimed herein is described in U.S. Pat. No. 3,764,135, issued Oct. 9, 1973, to Madison and titled "Empathy Game." That game operationalizes empathy as roletaking ability, and yields an empathy score that is a composite of the number of times that both members of a dyad are able to assume a given role and then select the same response from a given number of responses, for a given number of situations. Madison's work provides a method for testing the same individual against a number of other individuals, sequentially. That is, one's capability concerning roletaking behavior may vary from one partner to the another, and Madison shows how that variance can be measured. Madison's work also teaches roletaking in that it offers an opportunity for the same two individuals to replay the game, and to make different response selections during such replay, in order to achieve a more desirable outcome. However, Madison's approach is limited to measurement of the cumulative number of roletaking instances between two players. His method is also limited to the predetermined role choice options provided by the game. Significantly, Madison's game makes no provision for estimating the varying amounts of emotional distance between players' response choices.

While the just mentioned efforts of Madison are suggestive of the fact that (a) measurement, and (b) stimulation of roletaking ability are both matters of importance, substantial progress in this field has heretofore been limited due to the lack of adequate methodology in the field.

Therefore, with respect to measurement of emotional distance between individuals, there remains a great, unresolved need for a reliable methodology which can:

(i) measure the emotional distance between differing responses when individuals do not select the same response to a given situation;

(ii) enable individuals to create and interpret their own responses when there are no predetermined response choices available;

(iii) identify the issues over which individuals experience emotional distance;

(iv) utilize skills learned from use of the method to interpret and modify relationships in everyday life; and which ideally, can (v) measure the emotional distance between the selected responses of more than two individuals at the same time.

Particularly in Asian societies, such as in Japan, the ability to respond in a socially acceptable manner, not emotionally distant from others involved, is an important social and business skill. For example, in many business situations, it may be the potential "loss of face" and not the immediate business economic consequences which are paramount in business decisionmaking. Understanding the motivating forces behind such behavior in business decisions which maintain "face" or result in "loss of face" would be of particular advantage for businessmen dealing with such cultures.

Because the linkage between (i) the way that a particular behavior functions, (ii) the level of emotional distance that such behavior expresses, and (iii) the differences in interactants' perspectives on such behavior, given the same situation, has not heretofore been described, scientists and others have encountered serious difficulties in attempting to measure emotional distance between individuals as it relates to roletaking. Still more difficult has been the stimulation and development of roletaking ability in individuals. This problem has been exacerbated given the lack of any systematic method for developing such roletaking ability. Further, there exists a need for a system which enables the development of roletaking ability in a variety of settings.

In summary, with respect to roletaking, there currently exists in the art a great need for new and improved methods for:

1) measuring roletaking ability;

2) measuring the emotional distance between interactants' responses to a given situation when the parties do not take the role of the other;

3) identifying those issues that prevent particular combinations of persons from putting themselves in the role of others; and 4) providing strategies that interactants can use to improve their roletaking abilities in every-day life.

In addition, a critical need currently exists in the field of psychotherapy for a method which enables the development of roletaking ability. Moreover, it is likely that most social relationships could be significantly improved by increasing the roletaking abilities of the participants. Finally, for persons desiring to increase their own roletaking capabilities, or desiring to encourage roletaking development in others, there clearly exists a need for simple methods for measuring, understanding, stimulating and developing such roletaking ability.

SUMMARY OF THE INVENTION

I have invented, and disclose herein, a novel method for evaluation of the emotional distance between individuals.

My method recognizes that various forms of human social behavior can be described by use of discrete functional categories. Most simply, behavior can be described by use of two categories, IN-FACE or OUT-OF FACE behavior. However, in my method, I have found that it is more useful to use three basic categories for such description; those categories are (i) SOLIDARITY, (ii) NEGOTIATION, and (iii) NON-COMPLIANT behavior. With respect to the above described basic two behavior category sytem, IN-FACE behavior includes SOLIDARITY, and all other behavior categories are considered OUT-OF-FACE.

The three basic behavior categories set forth in the preceeding paragraph can be broken down into further defined sub-categories. Therefore, in one exemplary embodiment of my method, NEGOTIATION can be further defined as (a) an EXPLANATION, (b) COMPLIANCE, or (c) a REQUEST for further information. Also in that embodiment, NON-COMPLIANT behavior can be further defined as (a) DISAGREEMENT (or CHALLENGE), (b) AVOIDANCE, or (c) MAKING POINTS (or PUT-DOWN).

I have found that it is most useful to utilize seven functional categories and sub-categories (hereinafter "categories"), as they provide a convenient basis for the evaluation of behavior. Each of these seven categories of behavior expresses a different level of emotional distance between interactants. The emotional distance between individuals relates to the differences between their perspectives concerning the situations which they are faced with. These seven categories are (i) SOLIDARITY, (ii) EXPLANATION, (iii) COMPLIANCE, (iv) REQUEST, (v) CHALLENGE, (vi) AVOIDANCE, and (vii) MAKING POINTS.

An ordinal variable of emotional distance can be formed by arranging the seven above named categories of behavior according to the amount of emotional distance that each function expresses during social interaction.

SOLIDARITY includes AGREEMENT, and APPROVAL, which indicate no emotional distance between interactants.

NEGOTIATION includes behavior that functions in one of three ways:

First, polite EXPLANATION, that neither agrees with nor disagrees with the other, expresses a slight emotional distance between interactants. Explanation is not necessary when people are in agreement.

Second, COMPLIANT behavior is a polite response to a request and expresses slightly more emotional distance than explanation. When someone makes a request, compliance is expected.

Third, when a person REQUESTS a response from the other, his or her behavior expresses slightly more emotional distance than compliant behavior.

NON-COMPLIANT behavior includes behavior that functions in one of three ways:

First, an expression of DISAGREEMENT shows more emotional distance than request.

Second, AVOIDANCE, which is tinged with aggression, indicates more emotional distance than disagreement.

Third, MAKING POINTS behavior, that is behavior which tends to be rude or PUT someone DOWN, is the most emotionally distant behavior of all.

Thus, by identifying a particular behavior, and categorizing that particular behavior according to function, such as within the above described seven categories, the emotional closeness or distance between individuals can be estimated, based on particular preferred responses by the individuals.

One embodiment of the present invention involves a method of playing a game with two or more players wherein the players are provided with a number of hypothetical situations, are offered a set of possible responses (and may also be given an opportunity to create unique responses and provided with a set of rules for categorizing the responses by behavior type), so that the preferred responses can be evaluated in terms of the emotional distance between the various responses. The method used in the game includes providing to each player a score for the player's response selections wherein the total value of the game score is based upon the player's ability to take the role of the other player. The game winner is the player whose response choices indicate the least total emotional distance between his response choices and the response choices of the other players.

OBJECTS, ADVANTAGES, AND NOVEL FEATURES

From the foregoing, it will be evident to the reader that the primary object of the present invention resides in the provision of a novel, improved method for measuring the emotional distances between individuals in a given human interaction situation.

A related and important object of the present invention is to provide an improved game process for measuring the emotional distance between players' responses.

It is a feature of the present invention that descriptive, discrete, and categorically complete behavior types are established in order to create a methodology for measurement of the emotional distance between individuals is established.

It is an important advantage of the present invention that a discrete value scale is provided to distinguish between behavior type categories, thus enabling an easy method of measurement of emotional distance between individuals Another object of the present invention is to provide a method for evaluating and predicting the probable proportions of non-compliant behavior for particular combinations of persons who will be asked to work together on specific tasks.

A related object similar to the just mentioned object is to provide a game process that produces ratings of players' performances that can be reliably used for prediction of the probable proportions of non-compliant behavior for particular combinations of persons who will be asked to work together on specific tasks.

It is a feature of the present invention that the probability of non-compliant behavior can be quickly and easily evaluated by use of the game process provided.

A unique advantage of the present invention is that it provides an easily implemented method for prediction of the likely success of industrial project teams, based on the interpersonal behavior of the participants, and more specifically, based upon the emotional distance between the individuals involved.

Another object of the present invention is to provide a game process that can be used for teaching social interaction, both in education and in industry, and to students and professionals alike.

Another object of the present invention is to provide an improved, entertaining game process for measuring one or more players' roletaking ability.

Yet another object of the present invention is to provide a game process that produces data that can be used by researchers to learn more about social interaction.

A further object of the present invention is to provide a game process that produces ratings of a player's performance which are reasonably accurate.

A still further object of the present invention is to provide a game process in which skills learned by players can be used to improve their social and business relationships in their everyday lives.

An important advantage of the game provided by the present invention is that it is fun and entertaining to play, thus facilitating the learning process.

Other important objects, features, and additional advantages of the invention will be apparent to the reader from the foregoing and the appended claims and as the ensuing detailed description and discussion of the invention proceeds in conjunction with the accompanying drawing.

BRIEF DESCRIPTION OF THE DRAWINGS

In the drawing:

FIG. 2. depicts a response booklet for use in coding responses to particular situations.

FIG. 3 depicts the obverse side of a game card.

FIG. 4 depicts the reverse side of a game card.

FIG. 6A provides the obverse side of a scoring sheet.

FIG. 6B provides the reverse side of a scoring sheet.

DETAILED DESCRIPTION OF THE INVENTION

Figure 1:
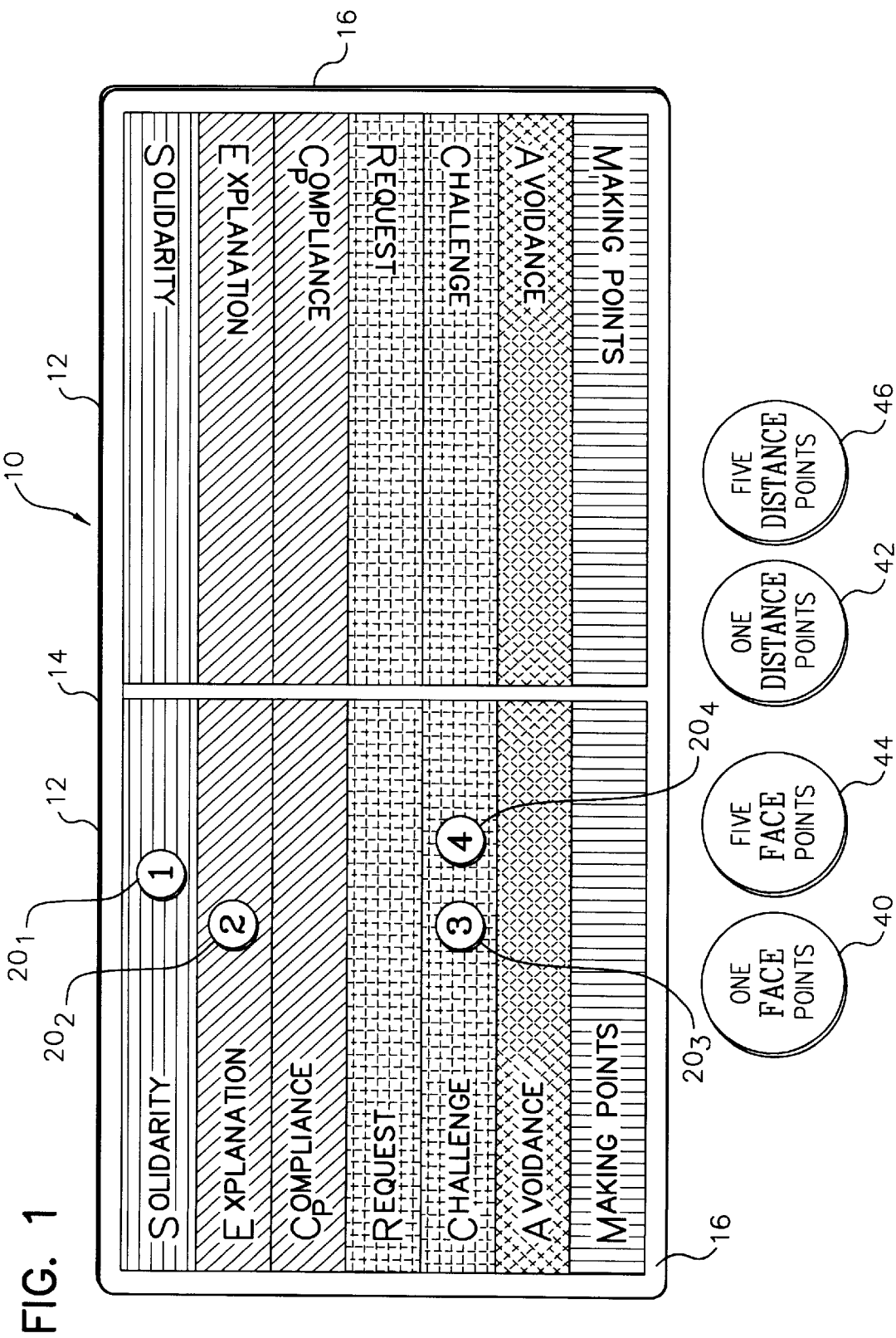
FIG. 1 depicts an embodiment of the game board and game pieces.

For the purpose of promoting an understanding of the principles of the invention, reference will now be made to the embodiment illustrated in the drawing and specific language will be used to describe the same. It will nevertheless be understood that no limitation of the scope of the invention is thereby intended, it being understood that the invention is defined by the appended claims and their legal equivalents; therefore any alterations and further modifications in the illustrated methods, and further applications of the principles of the invention as described and illustrated herein, shall be afforded the broadest protection provided by law.

Referring now to FIG. 1, there is illustrated game board 10. For convenience of carriage and storage, game board 10 may be provided in portions such as rectangular halves 12 which are joined together longitudinally at transversely disposed hinge 14 to form a single rectangular playing surface 16. The surface 16 of game board 10 is divided into seven elongate rectangular shaped playing spaces, each space bearing a symbol identifying the same, as follows:

S—Solidarity
E—Explanation
Cp—Compliance
R—Request
C—Challenge
A—Avoidance
M—Making Points Each of the above identified playing spaces represents one of seven mutually exclusive and exhaustive behavior types in which players responses are categorized. Preferably, and as depicted in this embodiment, the playing spaces are sequenced so that each playing space corresponds in position to a response category that functions on an increased or decreased level of emotional distance in accord with the playing space sequence, so as to form a gradient of emotional distance that is an ordinal variable. The value of this variable is useful in measuring (a) the emotional distance between game players' responses, and (b) cognitive differences between players' perspectives regarding the situation they are faced with.

The ordinal variable of emotional distance includes behaviors that function on different levels. The variable of emotional distance measures the degree to which people feel emotionally close or distant from one another. This emotional state can be exteranlly measured by categorization of a response provided by querying two or more individuals with regard to a set of social situations having multiple possible responses, and then comparing the behavior types characterized by the various responses obtained with respect to a scale with respect to which all possible behavior types being characterized have been categorized. Most simply, emotional distance can be described by behavior categories of IN-FACE or OUT-OF FACE. Behavior in SOLIDARITY is IN-FACE, and all other behavior categories are OUT-OF-FACE. Mor preferably, an emotional distance can be described on at least three different levels: (i) SOLIDARITY, (ii) NEGOTIATION, and (iii) NON COMPLIANCE. SOLIDARITY ("S"), indicates no measurable distance between the perspectives of the players and thereby no measurable emotional distance between the responses of the players, concerning the situation they are faced with.

NEGOTIATION includes three sub-categories of behavior types: (i) EXPLANATION ("E"), which expresses the lowest level of emotional distance between players; (ii) COMPLIANCE ("Cp"), which expresses an increased level of emotional distance; and (iii) REQUEST ("R"), which expresses a level of emotional distance that is greater than that expressed by COMPLIANCE.

NON-COMPLIANCE includes three sub-categories of behavior types: (i) CHALLENGE ("C"), which expresses more emotional distance than REQUEST; (ii) AVOIDANCE ("A"), which expresses more emotional distance than CHALLENGE; and (iii) MAKING POINTS ("M"), which indicates a greater level of emotional distance between players than any of the other behavioral type categories. The latter category, MAKING POINTS, also includes a "PUT-DOWN", as well as rude behavior. Thus, the game board provides a spatial indicator of the location of players board markers, thereby allowing the emotional distance between players to be measured and players' performance to be scored. The boundaries between the seven behavior types in which responses are categorized are defined according to how each particular category of response functions during social interaction. The differentiation between the seven response categories, and a method for determining the proper category of a given response, are described in greater detail below in the discussion regarding the RESPONSE CODING CHART.

To initiate game play, each player receives one board marker 20 that bears a number that indicates the playing order of the players and is movable on the game board. I prefer a round marker 20 that is about one (1.0) inch in diameter and one half (0.5) inch thick, when using a game board 10 with dimensions of about eleven (11) inches by seventeen (17) inches.

The player with board marker number one $20_1$ will draw the first situation card 22 (See FIG. 3) which on the reverse side bears a "SITUATION NUMBER" (See FIG. 4, which shows the reverse side 24 of the situation card 22 revealing a "SITUATION 1") that corresponds to a numbered set of RESPONSE OPTIONS in RESPONSE BOOKLET 26

(shown in FIG. 2). That player will then read aloud the situation posited by the situation card 22. For example, in FIG. 4, a SITUATION 1 is shown, and the player holding marker 20₁ would read the situation posed, namely, "Your friend tells you that your spouse is having an affair".

As noted above, each SITUATION NUMBER corresponds to a set of RESPONSE OPTIONS listed in the RESPONSE BOOKLET 26. As noted, each of the possible responses is classified by behavior category according to the seven categories discussed above, which categories also correspond to the seven playing spaces on the playing board 10. For SITUATION 1, the RESPONSE OPTIONS 1 include the following possible responses:

(1) "I think you should mind your own business," coded "M;"
(2) "Are you certain," coded "R;"
(3) "We have an open marriage," coded "E;"
(4) "I think you're right," coded "S;"
(5) "let's talk about something else" coded "A;" and
(6) "Other."

Figure 5:
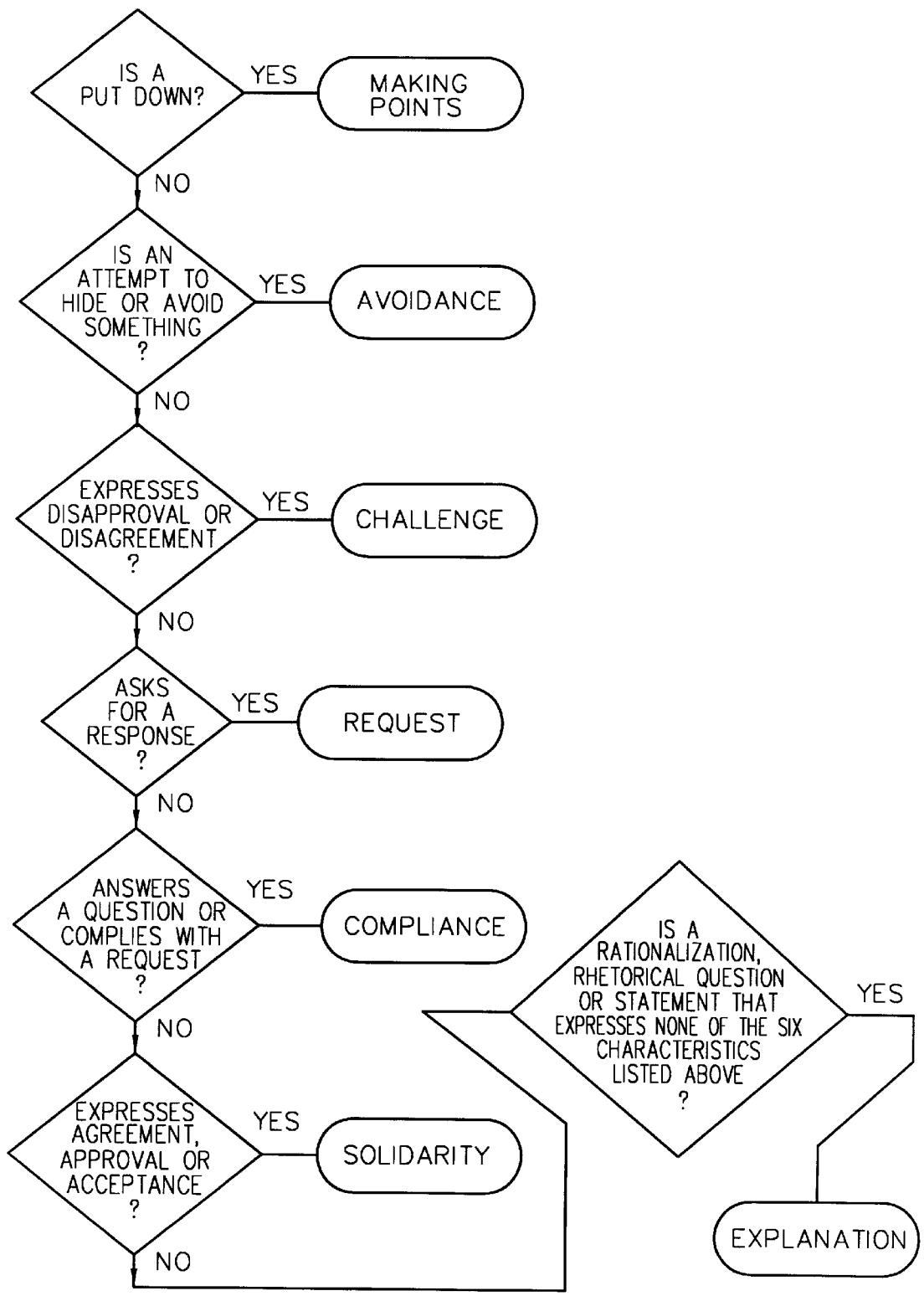
FIG. 5 provides a response coding chart.

Each player will then read the set of RESPONSE OPTIONS 1, silently, to his or her self. If the player finds an appropriate response, i.e., a response that he or she would actually make in the given the situation, then he/she will enter the code that follows the RESPONSE OPTION onto the CODE line 30 of score sheet 32, as shown in FIGS. 6A and 6B. If none of the precoded response options seem to be appropriate, i.e., none is the type of response that the player would ordinarily make, he or she may create his or her own response, record it on the RESPONSE line 34 of the score sheet 32. Then, the player must categorize the just created response by coding it. This is accomplished by asking the questions shown on the RESPONSE CODING CHART set forth in FIG. 5. The evaluation of the response is done by evaluating whether or not the player's response is:

1) a put down? If yes, it is M for Making Points. If no, is it:
2) an attempt to hide or avoid something? If yes, it is A for Avoidance. If no, is it:
3) an expression of disapproval or disagreement? If yes, it is C for Challenge. If no, is it:
4) a request for a response? If yes, it is R for Request. If no, is it:
5) a polite response or compliance to a request? If yes, it is Cp for Compliance. If no, is it:
6) an agreement, approval, or acceptance? If yes, it is S for Solidarity. If no then it is:
7) a believable statement, rationalization or rhetorical question that communicates information? If so, it is coded E for Explanation.

The each player will then enter the code of his response on the corresponding CODE line 30 of his score sheet 32.

As soon as all players have recorded their response codes in line 30 of their score sheets 32, each player will move his board marker 20₁, 20₂, 20₃, and 20₄ to the playing space that bears his or her response code for that play. For example, if the response code of player 1 is S for SOLIDARITY, then the player will move board marker 20₁ to the playing space marked S for SOLIDARITY.

Each player whose board marker 20 is on the same playing space as the majority of players is awarded one "FACE POINT" chip 40, also known as a "ROLE POINT". Each player whose board marker 20 is on any of the other coded playing space categories will receive a ONE DISTANCE POINT chip 42, also known as a "ROLE DISTANCE POINT", for each space that separates his board marker 20 from the board markers of the majority of players.

The definition of the majority which is actually utilized will depend upon the number of players. In the case of one player, that individual can compare his or her responses against the corresponding codes of a GAME PROFILE made up of the average codes of past game players, to establish the majority. Those skilled in the art to which this invention is directed will recognize that a variety of profiles can be created for different situations of game use, for different social characteristics of the players, and for differing social settings. Table I provides a typical GAME PROFILE for one type of user.

In the case of two players, a majority occurs when both players' board markers are on the same playing space. When their board markers are located on different playing spaces, each player will receive ONE DISTANCE POINT chip 42 for every playing space that separates his board marker from the other player's board marker. A unique situation occurs in the case of two players, since both players achieve the same score. This result simply underscores the equal responsibility that two individuals share for the relationship between them.

When there are more than two players a majority occurs on the playing space with the most board markers placed thereon. However, when there is no majority, a corresponding code from a GAME PROFILE can be used to establish a majority.

The play is completed when each player has received game chips 40 and 42 that represent the proximity of his board marker to that of the majority, in terms of playing spaces. Player number one will then place the first situation card face down on the bottom of the deck of SITUATION CARDS 22. Next, the player with board marker number 2 will repeat the just described performance of player number 1, and all players repeat the just described process of identifying a response, coding the same, moving board markers, and awarding FACE POINTS 40 and DISTANCE POINTS 42. For convenience and to minimize the number of chips that have to be handled during play, FIVE FACE POINT chips 44 and FIVE DISTANCE POINT chips 46 may also be provided. Play continues in this manner until the deck of situation cards has been exhausted.

At the end of the game process, each player will count the total number of points represented by his FACE POINT chips 40 and 44, and by his DISTANCE POINT chips 42 and 46, and record the totals on the reverse side 50 of his score sheet 32 in the space provided (see FIG. 6B).

TABLE I

GAME PROFILE

| PROFILE 1: SOCIAL CHARACTERISTICS: | |
|---|---|
| Sex: | 2 Males, 2 Females |
| Age: | Under 25 |
| Family Annual Income: | $20,000–$34,999 |
| Race: | Caucasian |
| Marital Status: | Never Married |
| Education: | Some College |

| RESPONSE CODE AVERAGE: | | | | |
|---|---|---|---|---|
| 1. E | 6. S | 11. C | 16. C | 21. R |
| 2. Cp | 7. C | 12. S | 17. M | 22. C |
| 3. E | 8. C | 13. E | 18. C | 23. C |
| 4. C | 9. Cp | 14. C | 19. R | 24. R |
| 5. Cp | 10. S | 15. S | 20. A | 25. Cp |

Then, the total DISTANCE POINT chips 42 is divided by the total FACE POINT chips 40 to get a game ratio score. The winner of the game is the player with the lowest ratio of DISTANCE POINTS to FACE POINTS.

For completeness, it may be helpful to review how the method of evaluating the emotional distance between individuals is determined during implementation of the game playing process. To begin the "FACE(tm)" game playing process, a deck is formed from an ordered series of SITUATION CARDS 22. A RESPONSE BOOKLET 26, a SCORE SHEET 32, a RESPONSE CODING CHART (FIG. 5) and a BOARD MARKER 20 is allocated to each player. The player who decides to be banker will take control of the FACE POINT chips 40 and 44, the DISTANCE POINT chips 42 and 46, and a GAME PROFILE. The player with BOARD MARKER 20 number one ($20_1$) will take the first SITUATION CARD 22, read it aloud to the other players and place it face up on the GAME BOARD 10. This SITUATION CARD 22 sets forth the situation that all of the players are faced with for that play. Each player then scans the coded responses in his RESPONSE BOOKLET 26. If he finds an appropriate response, then he will record the code of that response in the corresponding CODE 30 space on his SCORE SHEET 32. If he does not find an appropriate response then he will create his own response, record it on the RESPONSE LINE 34 provided on his SCORE SHEET 32. The response must be coded using the RESPONSE CODING CHART of FIG. 5. The response code must be recorded on the CODE 30 space on his SCORE SHEET 32.

After all players have recorded their RESPONSE CODES 30 on their SCORE SHEETS 32, each player will move his BOARD MARKER 20 to the playing space that bears the same CODE 30 as his response. Players must not discuss their responses until after their BOARD MARKERS 20 have been moved and the FACE POINT chips 40 and 44 and the DISTANCE POINT chips 42 and 46 have been obtained for a particular play. A player whose BOARD MARKER 20 is on the same playing space as the majority will receive one FACE POINT chip 40. A player whose BOARD MARKER 20 is on any of the other playing spaces will receive ONE DISTANCE POINT chip 42 for each playing space that separates his BOARD MARKER from the board marker(s) of the majority. Player number one will then place the SITUATION CARD 22 face down under the deck of SITUATION CARDS.

Each player, in turn, will repeat this process until the deck of SITUATION CARDS is exhausted. Each player will then count his FACE POINT chips 40 and 44, and his DISTANCE POINT chips 42 and 46, and record the totals on the back of his score sheet on the lines provided on the reverse side 50 of score sheet 32. Each player then divides his total DISTANCE POINT chips 40 and 44 by his total FACE POINT chips 42 and 46 to get a game ratio score. The winner of the game is the player with the lowest game ratio score.

Players who are not pleased with their game ratio scores can discuss the situations in which emotional distance occurred with the other players, to gain a better understanding of the others' perspectives. It is interesting to replay the game in an attempt to achieve a different game ratio score. The situations in which the face or role distance occurs can be identified by comparing the codes for each situation, among the players' score sheets.

The game process is an operationalization of a unified theory of social psychology which is useful on both micro and macro levels. The disclosed method for measuring the emotional distance between individuals in a preselected social situation, as may be represented by the categorization and profiling of players responses to game cards or the like, provides a tool for the prediction of emotional distance between individuals in any given human interaction between. It is a feature of the present invention and the game described to implement the invention that descriptive, discrete, and categorically complete behavior types are established in order to create a methodology for measurement of the emotional distance between individuals. The results of the game can be used to predict productivity in workgroups, as well as the tendency of workgroup members to like one another, as a result of their interaction, when the task to be performed by the workgroup requires them to deal with an emotionally distancing issue which is addressed by the game. When members of groups engage in more NON-COMPLIANT behavior, their productivity tends to fall, this tendency is measured by the method and game process described herein. This result is in agreement with everyday experience; those groups which tend to argue will likely get less done. The game results can also be used to predict patterns of dominance in group interaction. Dominance is revealed by a high number of REQUEST answers in comprison to the number of REQUEST answers provided by the other group members.

It will be understood that some variations of the game process can be made without departing from the teachings and principles described herein. Also, counting arrangements other than the means described above can be used for scoring the psycho-social game process. For example, a computerized embodiment of the invention could be programmed to allow player access, accumulate the scores, compare one players' scores with other player's scores, generate game profiles, compare players' scores with profiles, printout an analysis of these results for each player's responses and accumulate a data base.

Also, it will be understood that the method and game process taught herein, in its entirety as well as in portions thereof, may be useful in a wide variety of applications, examples of which are set forth below.

EXAMPLE I

Behavioral Science

Behavioral scientists may use the behavior response categories and coding process taught herein to relate such variables as productivity, dominance, self-esteem. For example, "liking," i.e., how much people tend to like one another as a result of their interaction, may be examined. Also, use of the response categories may lead to evaluations of and classification of particular proportions of specific categories of observable behavior.

EXAMPLE II

Industry Productivity

Industry may use the method and/or the game taught herein to improve the productivity of work groups. That is, the emotional distance amongst workgroup members can be evaluated, and, if desirable, workgroup selection can be managed so as to minimize the likelihood of friction generated by emotionally distant members (i.e., high NON-COMPLIANCE results from DISAGREEMENT, AVOIDANCE, and MAKING POINTS).

EXAMPLE III

Law

Trial lawyers may use the behavior categorization system for jury selection, so as to attempt to pick individuals whose answers would predict minimal emotional distance from the desired result. Also, the method may be useful for negotiators in dispute resolution, in assisting in understanding the behavior exhibited, and therefor providing a basis for addressing the differences between parties.

EXAMPLE IV

Education

Educators may use the game for teaching human relations. The game may be of particular interest to students of such subjects as social science, law, medicine, social services, diplomacy, sales, advertising and parenting.

This invention may be embodied in still other specific forms without departing from the spirit or essential characteristics thereof. It will be appreciated by those skilled in the art that the methods illustrated herein may be embodied in a machine implemented method susceptible of execution on a data processor without departing from the scope and spirit of the claimed invention. Further, it can be readily appreciated that the number of categories utilized may be varied upward or downward. For example, only the three categories of SOLIDARITY, NEGOTIATION, and NON-COMPLIANT behavior may be used to some advantage. Also, use of simply two categories, IN-FACE and OUT-OF-FACE, will be useful in other situations. Likewise, a number of categories in excess of seven may be utilized. Alternatively, subdivisions of the seven categories (or other chosen number of categories) provided may be utilized to further define degrees of emotional distance between individuals. And, although the order of categories illustrated provides an incremental scale of emotional distance between individuals, the categories could be otherwise ordered and the mathematical computations performed to achieve a similar measurement of emotional distance between individuals, without varying from the teachings herein. The present embodiments are therefore to be considered in all respects as illustrative and not restrictive, the scope of the invention being indicated by the appended claims rather than by the foregoing description. All changes which come within the meaning and range of equivalency of the claims are therefore intended to be embraced therein.

I claim:

1. A method for measurement of the emotional distance between two or more preselected individuals in one or more preselected social situations, said method comprising:
    (a) selecting a description of one or more social situations for presentation in a tangible medium of expression;
    (b) presenting via a tangible medium of expression said description of said one or more social situations to each of such two or more preselected individuals, and then
    (c) presenting each of such two or more preselected individuals with a plurality of possible responses to each of said one or more social situations;
    (d) recording in a tangible medium of expression the actual response provided by each of such two or more preselected individuals to each of said one or more social situations, wherein each actual response to each of said one or more social situations is selected from said plurality of possible responses to each of said one or more social situations, and wherein each actual response is recorded in a preselected behavior type category;
    (e) comparing said behavior types by measuring the distance, on an ordinal scale including two or more preselected behavior type categories, between any of said two or more preselected behavior type categories into which the answers provided by each of said individuals in actual response to said one or more social situations has been recorded.

2. The method of claim 1, wherein the step of presenting, via a tangible medium of expression, said description of said one or more social situations to two or more preselected individuals, is accomplished by (a) recording said description of one or more social situations in a medium selected from the group comprising (i) printed cards, (ii) pen and paper, and (iii) a general purpose computer with data base, and (b) showing such recording to each of said two or more preselected individuals.

3. The method of claim 1, wherein the step of presenting, via a tangible medium of expression, a plurality of possible responses to one or more social situations to two or more preselected individuals, is accomplished by (a) recording said description of said possible responses in a medium selected from the group comprising (i) printed cards, (ii) pen and paper, and (iii) a general purpose computer with data base, and (b) showing such recording to each of said two or more preselected individuals.

4. The method of claim 1, wherein the step of recording, in a tangible medium of expression, the actual response provided by each of such two or more individuals by a preselected behavior type, is accomplished by recording in a medium selected from the group comprising (i) printed score cards, (ii) pen and paper, and (iii) a general purpose computer with data base.

5. The method of claim 1, wherein
    the step of comparing said behavior type categories by measuring the distance, on an ordinal scale including two or more preselected behavior type categories, between any of said two or more preselected behavior type categories into which the answers provided by each of said individuals in actual response to said one or more social situations has been recorded,
    is accomplished by a method selected from the group comprising (i) display on a playing board, (ii) manual computation with pen and paper, and (iii) mathematical calculations performed on a general purpose computer, using data stored in a data base program.

6. The method of claim 1, wherein said preselected behavior type categories comprise
    (a) IN-FACE behavior, and
    (b) OUT-OF-FACE behavior.

7. The method of claim 1, wherein said possible responses comprise at least three behavior type categories.

8. The method of claim 7, wherein said at least three behavior type categories comprise behavior type categories:
    (a) SOLIDARITY,
    (b) NEGOTIATION, and
    (c) NON-COMPLIANT behavior.

9. The method of claim 8, wherein said NEGOTIATION behavior type category further comprises the behavior type categorized as EXPLANATION.

10. The method of claim 8 or claim 5, wherein said behavior type category identified as NEGOTIATION further comprises the behavior type categorized as COMPLIANCE.

11. The method of claim 8, or claim 9, or claim 10, wherein said NEGOTIATION behavior type category further comprises the behavior type categorized as a REQUEST.

12. The method of claim 8, wherein said behavior type categorized as NON-COMPLIANT further comprises the behavior type categorized as CHALLENGE.

13. The method of claim 8 or claim 12, wherein said NON-COMPLIANT behavior type further comprises the behavior type categorized as AVOIDANCE.

14. The method of claim 8 or claim 12 or claim 13, wherein said NON-COMPLIANT behavior type further comprises the behavior type categorized as MAKING POINTS.

15. A method for measurement of the emotional distance between two or more preselected individuals in one or more preselected social situations, said method comprising:

(a) selecting a description of one or more social situations for presentation in a tangible medium of expression;

(b) presenting via a tangible medium of expression said description of said one or more social situations to two or more preselected individuals, and then (c) presenting each of such two or more preselected individuals with a plurality of possible responses to each of said one or more social situations;

(d) recording in a tangible medium of expression the actual response provided by each of such two or more preselected individuals to each of said one or more social situations, wherein each actual response to each of said one or more social situations is selected from said plurality of possible responses to each of said one or more social situations, and wherein each actual response is recorded in a preselected behavior type category;

(e) comparing said behavior types by measuring the distance, on an ordinal scale including at least seven preselected behavior type categories, between any of said at least seven preselected behavior type categories into which the answers provided by each of said individuals in actual response to said one or more social situations has been recorded, and (f) wherein said at least seven behavior type categories comprise a set of at least the following behavior type categories:
(i) SOLIDARITY;
(ii) EXPLANATION;
(iii) COMPLIANCE;
(iv) a REQUEST;
(v) a CHALLENGE;
(vi) AVOIDANCE; and
(vii) MAKING POINTS.

16. The method of claim 15, wherein the step of presenting, via a tangible medium of expression, said description of said one or more social situations to two or more preselected individuals, is accomplished by (a) recording said description of one or more social situations in a medium selected from the group comprising (i) printed cards, (ii) pen and paper, and (iii) a general purpose computer with data base, and (b) showing such recording to each of said two or more preselected individuals.

17. The method of claim 15, wherein the step of presenting, via a tangible medium of expression, a plurality of possible responses to one or more social situations to two or more preselected individuals, is accomplished by (a) recording said description of said possible responses in a medium selected from the group comprising (i) printed cards, (ii) pen and paper, and (iii) a general purpose computer with data base, and (b) showing such recording to each of said two or more preselected individuals.

18. The method of claim 15, wherein the step of recording, in a tangible medium of expression, the actual response provided by each of such two or more individuals by a preselected behavior type, is accomplished by recording in a medium selected from the group comprising (i) printed score cards, (ii) pen and paper, and (iii) a general purpose computer with data base.

19. The method as described in claim 15, wherein a value is assigned to each of said behavior type categories along an ordinal variable, said value determinant of the sequence and relation of each of said behavior type categories one to another, so as to establish a distance value between said behavior type categories, each from the other.

20. The method of claim 19, wherein the step of comparing said behavior type categories by measuring the distance, on an ordinal scale including two or more preselected behavior type categories, between any of said two or more preselected behavior type categories into which the answers provided by each of said individuals in actual response to said one or more social situations has been recorded, is accomplished by a method selected from the group comprising (i) display on a playing board, (ii) manual computation with pen and paper, and (iii) mathematical calculations performed on a general purpose computer, using data stored in a data base program.

21. The method as described in claim 20, further comprising analyzing the distance between said behavior type categories of said preferred responses, of each of said two or more preselected individuals, one from the other, to each preselected social situation.

22. The method as set forth in claim 21, further comprising analyzing the average value of the behavior type categories selected in response to each preselected social situation, for all of said two or more preselected individuals being evaluated.

23. The method as set forth in claim 22, wherein each of the behavior type categories which are identified are ordered with respect to the other, in a set of variables comprising the preselected behavior type categories, so that each succeeding behavior type category along an ordinal direction corresponds to a behavior type category that functions on an increased level of emotional distance, so as to form a gradient between behavior type categories along an ordinal variable, so that emotional distance is measured by determining the distance between the location of said behavior type categories along said ordinal variable.

24. A game process for measuring the emotional distance between two or more players' responses to a set of preselected social situations, wherein said game process comprises the steps of:

(a) selecting a description of one or more social situations for presentation in a tangible medium of expression;

(b) presenting via a tangible medium of expression said description of said one or more social situations to two or more preselected game players, and then (c) presenting each of such two or more preselected game players with a plurality of possible responses to each of said one or more social situations;

(d) recording in a tangible medium of expression the actual response provided by each of such two or more preselected game players to each of said one or more social situations, wherein each actual response to each of said one or more social situations is selected from said plurality of possible responses to each of said one or more social situations, and wherein each actual response is recorded in a preselected behavior type category;

(e) analyzing each of such preferred responses to determine the quality of such preferred responses by categorizing each preferred response to determine a response code, wherein each of said responses are categorized by behavior type and each behavior type corresponds to a response code; and (f) comparing said behavior types by measuring the distance between said categorized behavior types, each of which categorized behavior types represent said preferred responses from each of such preselected game players, on an ordinal scale;

(g) wherein said at least seven categories are provided for said behavior type categories, and wherein said behavior type categories comprise a set of at least the following:

(i) SOLIDARITY;
(ii) EXPLANATION;
(iii) COMPLIANCE;
(iv) a REQUEST;
(v) a CHALLENGE;
(vi) AVOIDANCE; and
(vii) MAKING POINTS.

25. The method of claim 24, wherein the game process is played on a game board having a plurality of playing spaces comprising a set of behavior type categories, said behavior type categories ordered on said board in a graduated relationship so as to represent increasing levels of emotional distance between said possible response choices of said preselected game players, so that the distance between the playing spaces corresponds to the distance between behavior type categories being selected from said possible responses.

26. The method of claim 25, wherein each of said preselected game players is provided with a board marker for indicating said player his position on the game board, and wherein the game process further comprises the step of moving each player's board marker to the playing space corresponding to that of said player's preferred response code corresponding to the behavior type category selected by that player in response to a preselected social situation which is presented.

27. The method of claim 26, wherein the game process further comprises awarding one FACE POINT chip to each preselected game player whose board marker position corresponds to the position on said game board of a majority of the board markers of all of said preselected game players.

28. The method of claim 27, wherein the game process further comprises awarding one DISTANCE POINT chip to each preselected game player for each space on said board by which that game player's board marker position is located away from the board marker position of the majority of game players, so that the DISTANCE POINT chip represents the emotional distance of a selected game player from the position of the majority of the game players.

29. The method of claim 28, wherein each DISTANCE POINT chip corresponds with one playing space of distance between (a) the behavior type category selected by a preselected game player as indicated by his response code, and represented by the location of his board marker position, and (b) the behavior type category selected by the majority of game players, as indicated by the response code of the majority of game players, and as represented by the location of board marker positions of the majority of game players.

30. The method of claim 29, wherein each FACE POINT chip awarded corresponds with agreement between (a) the response code of the preselected game player and (b) the response code of the majority of preselected game players, (c) so that there is a common location between the board marker position of a preselected game player and the board marker positions of the majority of preselected game players.

31. The method of claim 30, wherein said game board surface comprises seven playing spaces, and wherein each of said seven playing spaces corresponds to a preselected behavior type category.

32. The method of claim 31, wherein each playing space contains a symbol indicator that corresponds to a preselected behavior type category.

33. The method of claim 32, wherein each behavior type category functions as an indicator of a preselected game player's externally observable response to a preselected social situation, so that by comparison between behavior type categories which are chosen by various players amongst a preselected group of game players, an indicia of the emotional distance between such players, when they face the same social situation, can be determined.

34. The method as set forth in claim 33, wherein the said seven playing spaces correspond to a gradient of seven behavior type categories, along which gradient an indicia of emotional distance between preselected game players may be determined.

35. The method as set forth in claim 34 wherein said seven levels of behavior type categories correspond to seven mutually exclusive and exhaustive functional categories of behavior types.

36. The method as set forth in claim 35, wherein said seven playing spaces correspond to the behavior type categories comprising (i) SOLIDARITY;
(ii) EXPLANATION;
(iii) COMPLIANCE;
(iv) a REQUEST;
(v) a CHALLENGE;
(vi) AVOIDANCE; and
(vii) MAKING POINTS.

37. The method of claim 36 wherein the number of REQUEST response codes accumulated by a preselected game player corresponds with the amount of dominance by that preselected game player which is externally observed by each of the other of said preselected game players.

38. The method of claim 37, wherein an increase in the NON-COMPLIANT behavior type category response codes accumulated by a preselected game player corresponds with a predicted decrease in productivity of an individual.

39. The method of claim 39, wherein an increase in the NON-COMPLIANT behavior type category response codes accumulated by a preselected game player corresponds to a dislike amongst preselected game players.

* * * * *